(12) United States Patent
Ingel et al.

(10) Patent No.: US 10,452,263 B2
(45) Date of Patent: Oct. 22, 2019

(54) PATIENT FACE AS TOUCHPAD USER INTERFACE

(71) Applicant: Biosense Webster (Israel) Ltd., Yokneam (IL)

(72) Inventors: Moshe Ingel, Haifa (IL); Ohad Inbar, Modiin (IL); Akram Zoabi, Kafar Misr (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 94 days.

(21) Appl. No.: 15/703,418

(22) Filed: Sep. 13, 2017

(65) Prior Publication Data
US 2019/0076197 A1    Mar. 14, 2019

(51) Int. Cl.
| | |
|---|---|
| *G06F 3/0488* | (2013.01) |
| *A61B 34/20* | (2016.01) |
| *G06K 9/00* | (2006.01) |
| *G06T 7/33* | (2017.01) |
| *G06T 17/00* | (2006.01) |
| *G16H 30/40* | (2018.01) |
| *G06F 3/038* | (2013.01) |

(Continued)

(52) U.S. Cl.
CPC .......... *G06F 3/04886* (2013.01); *A61B 34/20* (2016.02); *G06F 3/038* (2013.01); *G06F 3/0346* (2013.01); *G06F 3/03547* (2013.01); *G06K 9/00228* (2013.01); *G06T 7/33* (2017.01); *G06T 17/00* (2013.01); *G16H 30/40* (2018.01); *A61B 2034/2051* (2016.02); *A61B 2034/2065* (2016.02)

(58) Field of Classification Search
CPC . A61B 34/20; A61B 2034/2065; G06T 17/00; G06T 7/33
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron |

(Continued)

FOREIGN PATENT DOCUMENTS

WO    9605768    2/1996

OTHER PUBLICATIONS

Kaggelides, et al. "Locating the Eyes in CT Brain Scan Data" Proceedings of the 6th International Conference on Industrial and Engineering Applications of Artificial Intelligence and Expert Systems, 1993, pp. 507-517.

*Primary Examiner* — Michelle L Sams
(74) *Attorney, Agent, or Firm* — Volpe and Koenig, P.C.

(57) ABSTRACT

A method of registering a patient face and using it as a touchpad interface is provided. The method includes steps of acquiring a three-dimensional anatomical image of a patient face, identifying multiple anatomical points at the predefined locations on the patient face in a first coordinate system and assigning at least one function to at least one predefined location, receiving multiple positions in a second coordinate system at the respective predefined locations on the patient face, registering the first and second coordinate systems, by correlating between the positions and the respective anatomical points on the patient face, triggering a command corresponding to the at least one assigned function and communicating the command to an electronic device. A system for registering a patient face by the method is described.

19 Claims, 4 Drawing Sheets

(51) Int. Cl.
*G06F 3/0346* (2013.01)
*G06F 3/0354* (2013.01)

(56) References Cited

U.S. PATENT DOCUMENTS

| | | |
|---|---|---|
| 6,484,118 B1 | 11/2002 | Govari |
| 6,560,354 B1 | 5/2003 | Maurer, Jr. et al. |
| 6,618,612 B1 | 9/2003 | Acker |
| 6,632,089 B2 | 10/2003 | Rubbert et al. |
| 6,690,963 B2 | 2/2004 | Ben-Haim |
| 2002/0065455 A1 | 5/2002 | Ben-Haim |
| 2002/0105623 A1 | 8/2002 | Pinhanez |
| 2003/0120150 A1 | 6/2003 | Govari |
| 2004/0068178 A1 | 4/2004 | Govari |
| 2013/0169827 A1* | 7/2013 | Santos ............... H04N 5/23229 348/207.1 |
| 2015/0013689 A1* | 1/2015 | Shackelford ......... A61B 5/0073 128/853 |
| 2015/0220154 A1 | 8/2015 | Midholt |
| 2015/0268799 A1* | 9/2015 | Starner ................ G02B 27/017 345/175 |
| 2016/0042557 A1* | 2/2016 | Lin ........................... G06T 7/73 345/426 |
| 2017/0252108 A1* | 9/2017 | Rios ....................... G06F 19/00 |

\* cited by examiner

PATIENT FACE AS TOUCHPAD USER INTERFACE

SUMMARY

In an aspect, the invention relates to a method for registering a patient face and using it as a touchpad user interface. The method comprises acquiring a three-dimensional anatomical image of a patient face and identifying multiple anatomical points corresponding to respective predefined locations on the patient face in a first coordinate system and assigning at least one function to at least one predefined location. The method further comprises receiving multiple positions in a second coordinate system at the respective predefined locations on the patient face and registering the first and second coordinate systems, by correlating between the positions and the respective anatomical points on the patient face. The method also comprises triggering a command corresponding to the at least one assigned function, and communicating the command to an electronic device.

In an aspect, the invention relates to a system for registering a patient face and using it as a touchpad user interface. The system comprises: a registration tool, which comprises a position sensor of a position-tracking system, which is configured to acquire multiple positions in a second coordination system by positioning the registration tool at respective predefined locations on a patient face; and a processor. The processor is configured to identify, in a three-dimensional anatomical image of the patient face, multiple anatomical points corresponding to the respective predefined locations in a first coordinate system and to assign at least one function to at least one predefined location on the patient face. The processor is also configured to receive the multiple positions measured in the second coordinate system, and register the first and second coordinate systems, by correlating between the positions and the respective anatomical points on the patient face. The processor is also configured to retrieve a command corresponding to the at least one assigned function.

BRIEF DESCRIPTION OF THE DRAWINGS

The following detailed description of the embodiments of the present invention will be better understood when read in conjunction with the appended drawings. For the purpose of illustration, there are shown in the drawings embodiments which are presently preferred. It is understood, however, that the invention is not limited to the precise arrangements and instrumentalities shown. In the drawings.

DETAILED DESCRIPTION OF THE PREFERRED EMBODIMENTS

The present disclosure relates generally to methods of utilizing a patient's face as a user interface to facilitate usability of registration equipment.

As used herein, the term "registration" refers to a process for determining the spatial relationship between body parts and a three-dimensional (3D) computer image constructed, for example, from the preoperative computer tomography (CT) scan. Surgical navigation systems are used to guide the physician movements during medical procedures.

In certain medical procedures, such as Ear-Nose-Throat (ENT) surgery, an anatomical image of relevant organs may be registered with a coordinate system of a position tracking system. Using the registration, a surgical tool fitted with a position sensor may be navigated to the treated organs, and can be visualized overlaid on the anatomical image. In principle, pre-operative registration may be carried out using an external registration tool fitted with a position sensor of the position tracking system. Such a tool could be applied to the preselected locations on the patient face (e.g., forehead, and centers of the two cheeks). The anatomical image could then be registered to the coordinate system of the position tracking system based on the measured positions of tissue at the preselected locations.

Computerized tomography imaging systems and position-tracking systems are known in the art. Methods to register medical images are described, for example, in U.S. Pat. No. 6,560,354 and U.S. patent application Ser. No. 15/674,380, which are incorporated herein by reference as if fully set forth. U.S. Pat. No. 6,560,354 describes apparatus and method for registration of images to physical space using a weighted combination of points and surfaces. An image of a patient taken through X-ray computed tomography is registered to physical measurements taken on the patient's body. Different parts of the patient's body are given different numerical weights; for example, if bone measurements are deemed to be more accurate than skin measurements, the bones can be given a higher weight than the skin. The weights are used in an iterative registration process to determine a rigid body transformation function.

U.S. patent application Ser. No. 15/674,380 describes a method and an apparatus for Ear-Nose-Throat (ENT) registration. The method includes receiving a computerized tomography (CT) image of voxels of a subject's head, and analyzing the image to identify respective locations of the subject's eyes in the image, so defining a first line segment joining the respective locations. The method also includes identifying a voxel subset overlaying bony sections of the head, lying on a second line segment parallel to the first line segment and on a third line segment orthogonal to the first line segment. A magnetic tracking system configured to measure positions on the subject's head is activated, and a probe, operative in the system is positioned in proximity to the bony sections to measure positions of a surface of the head overlaying the bony sections. A correspondence between the positions and the voxel subset is formed, and a registration between the CT image and the magnetic tracking system is generated in response to the correspondence.

Physicians, such as Ear-Nose-Throat (ENT) physicians, often perform medical procedures without the assistance of a nurse. For example, in the case of ENT mapping and registration procedures, the ENT physician performs procedures in sterile environments, and is himself/herself scrubbed and sterilized. Thus, it is inconvenient for the physician to remove gloves to perform the registration and touch a mouse or keyboard during the procedure. However, the physician still needs to use the computer and is often alone with the equipment. Therefore, physicians need an improved system that facilities computer use during procedures when nurses are not present in the room.

The proposed system utilizes the patient's face as a touchpad user interface. For example, during an ENT registration procedure, the physician (who is scrubbed and sterilized) will not need to remove gloves to operate a mouse or keyboard. Instead, the physician can use the patient's face and other parts of the head as a touchpad interface.

System Description

Figure 1:
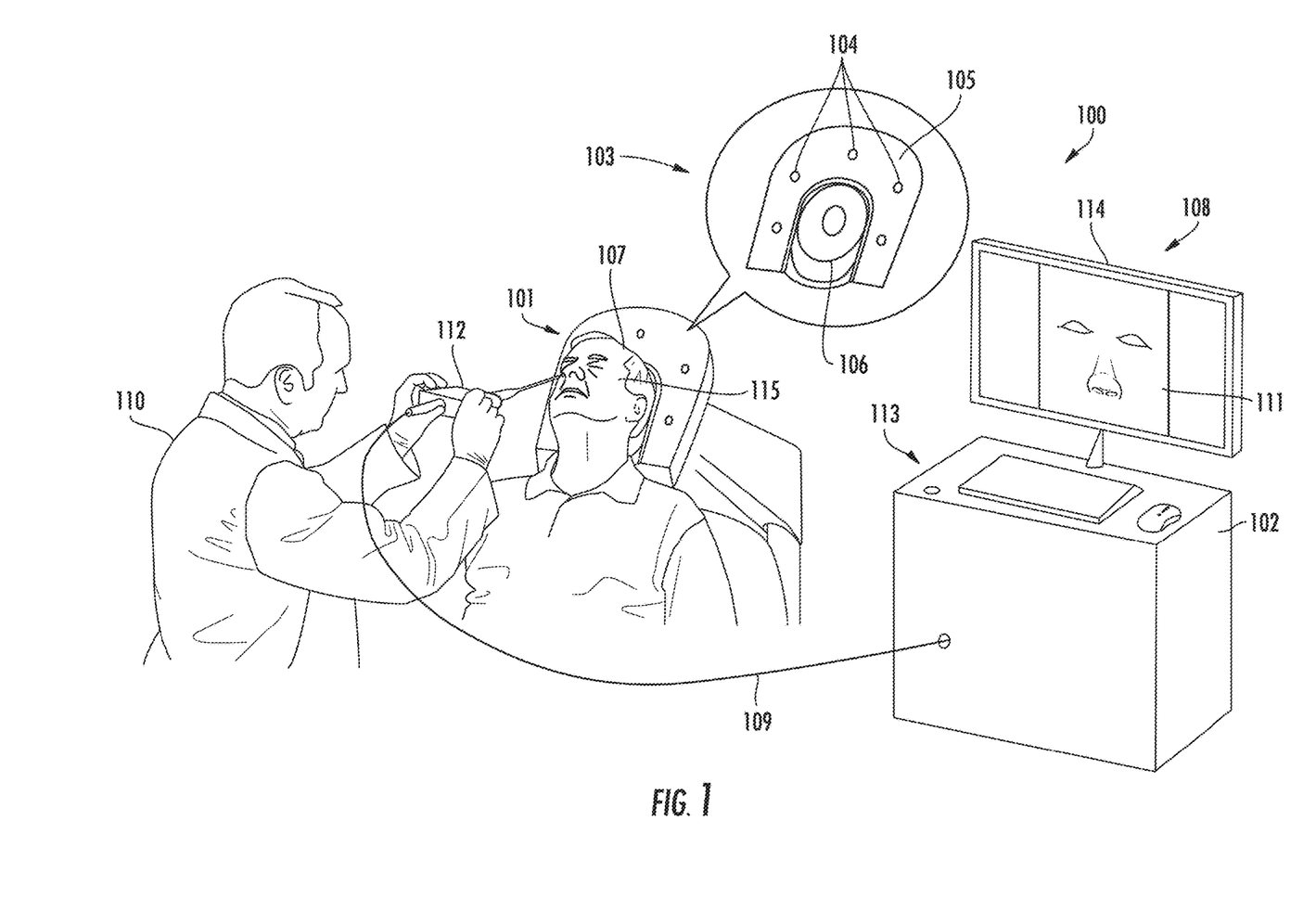
FIG. 1 is a schematic drawing of a surgical system, in accordance with an embodiment of the present invention.

FIG. 1 is a schematic drawing of a surgical system 100, in accordance with an embodiment of the present invention. System 100 comprises a magnetic position tracking system, which is configured to track the position of one or more position sensors (not shown) in the head of a patient 101. The magnetic position tracking system comprises magnetic field generators 104 and one or more position sensors. The position sensors generate position signals in response to the sensed external magnetic fields from the field generators and enable a processing device 102 to map the position of each sensor in the coordinate system of the position tracking system as described herein.

The methods of position system is known in the art and described in U.S. Pat. Nos. 5,391,199; 6,690,963; 6,484,118; 6,239,724; 6,618,612 and 6,632,089; in International Patent Publication No. WO 96/05768; and in U.S. Patent Application Publications 2002/0065455; 2003/0120150 and 2004/0068178, all of which are incorporated herein by reference as if fully set forth. Position system 100 comprises a location pad 103, which comprises multiple field generators 104 fixed to a frame 105. Referring to FIG. 1, pad 103 comprises five field generators 104, but any other suitable number of field generators 104 can be used. Pad 103 comprises a pillow 106 placed under a head of patient 101, such that generators 104 are located at fixed known positions external to the patient. System 100 further comprises a console 108, which comprises a driver circuit (not shown) configured to drive field generators 104 with suitable signal so as to generate magnetic fields in a predefined working volume around head 107.

In an embodiment, system 100 comprises a registration tool. The registration tool 112 may be a handheld wand. Wand 112 may be used by system 100 for registering the coordinate system of the magnetic tracking system with that of pre-acquired computerized tomography (CT) image. The registration tool 112 is configured to acquire position measurement.

In an embodiment, processor 102 is a general-purpose computer comprising suitable front and interface circuits for receiving data from external sources, as well as measurements from the position sensor of wand 112 via cable 109, and for controlling other components of system 100. Console 108 further comprises input devices 113 and a screen display 114, which is configured to display the data.

Figure 4:
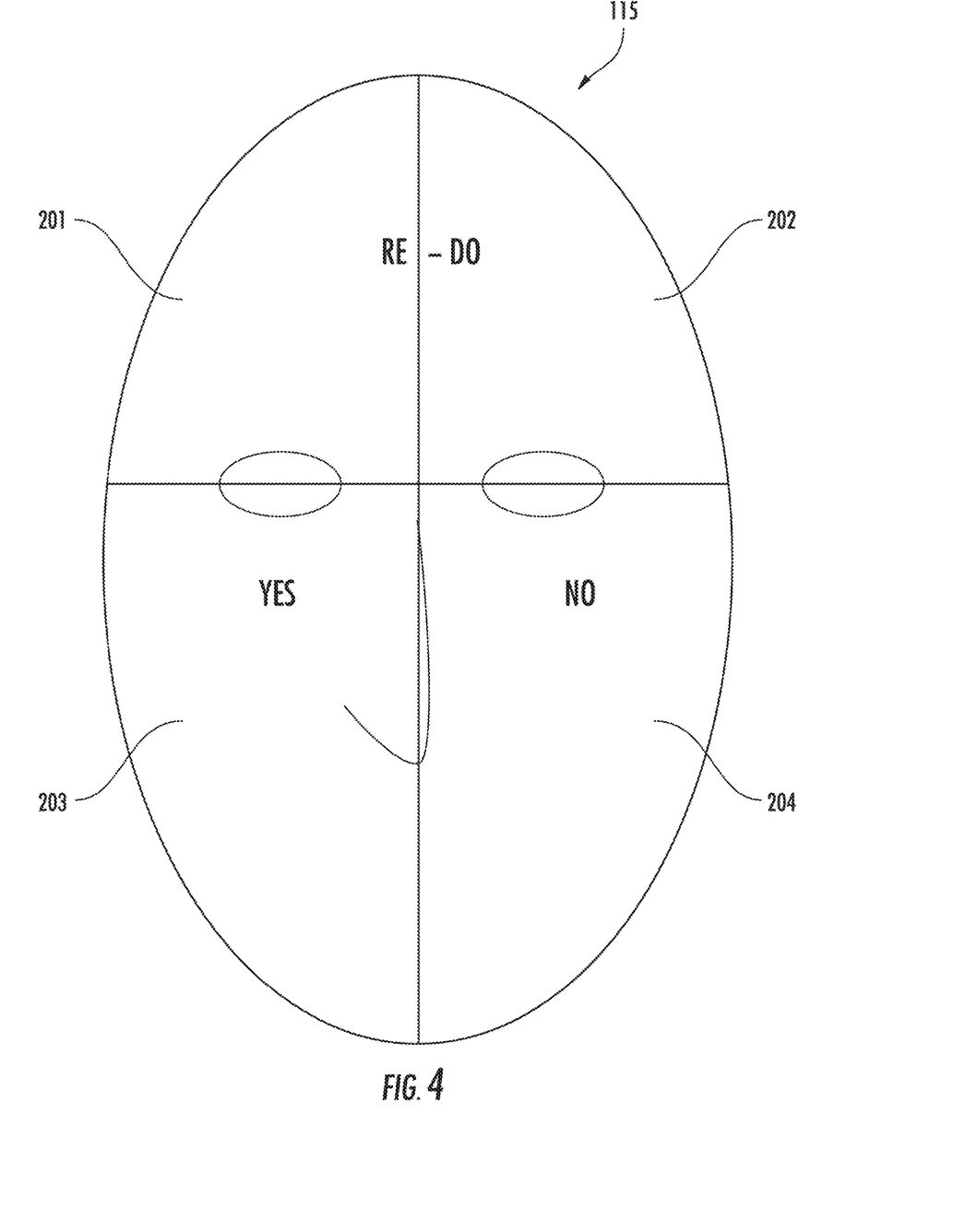
FIG. 4 is a schematic drawing of the patient face used as a user interface to control equipment.

A physician 110 may place wand 112 to a predefined location on patient head 107. Each predefined location is a portion of face 115. The predefined location may be any one of quarters or quadrants of the face: upper-right quadrant, upper-left quadrant, lower-right quadrant, or lower-left quadrant, or any other suitable identifiable portion. Exemplary predefined locations of patient face 115 are illustrated in FIG. 4.

In an embodiment, processing device 102 receives a computerized tomography (CT) image 111 obtained using an external CT system (not shown).

Figure 3:
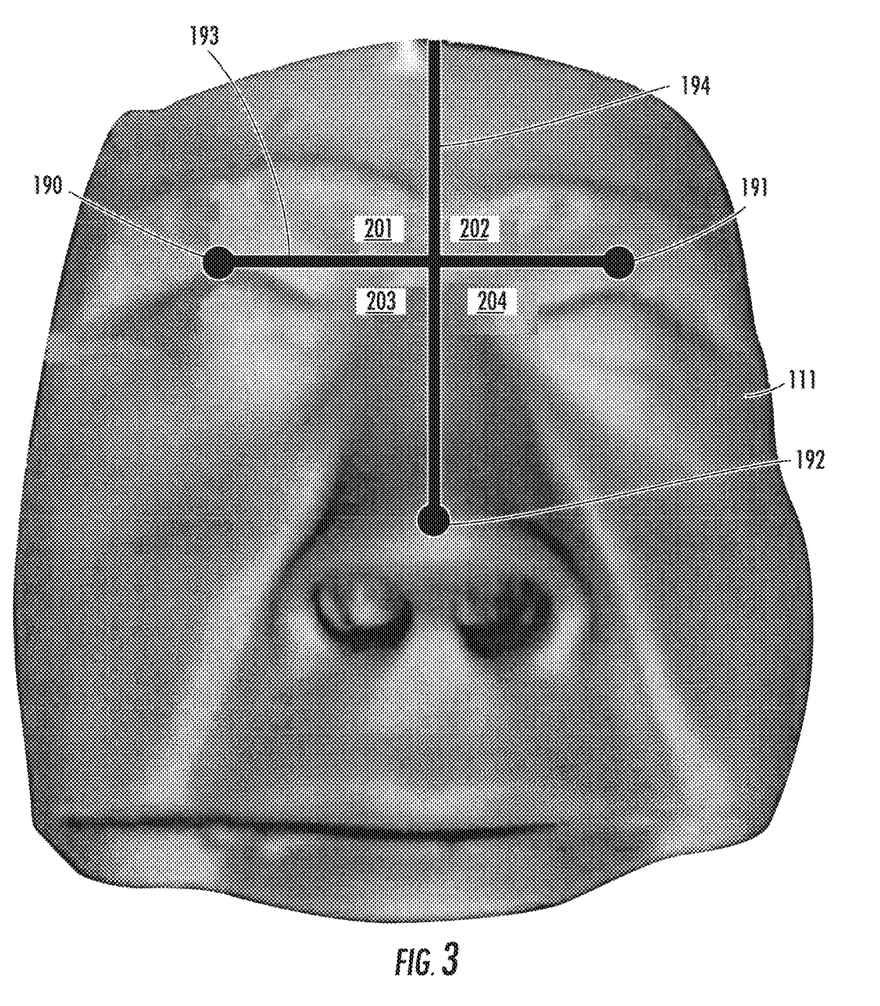
FIG. 3 is a schematic drawing of the three-dimensional computer tomography image of the patient face used in the registration method illustrated in FIG. 2.

Processing device 102 may use image 111 to project a surface image of patient face 115 on input device 113 or to screen display 114 to assist the physician and/or serve as a user interface. Processing device 102 may distinguish different portions of the CT image 111. Processing device 102 may identify a nose, or eyes, using any suitable criterion or technique such as hounsfield unit (HU). Processing device 102 may analyze the CT image 111 to identify and may define different portions of the face. The different portions of the face may be quadrants 201, 202, 203 and 204 as shown in FIG. 3.

In an embodiment, when placed at a predefined location on the patient face, wand 112 is configured to generate position signals indicative of this predefined location in the coordinated system of the magnetic position tracking system. The processing device 102 stores position signals or points acquired in predefined locations in each of the quadrants 201, 202, 203 and 204. The minimum number of points may be respectively 20, 20, 12, and 12. However, the minimum number of points may be lesser or greater than any one of these values, and may be the same or different value for all quadrants.

In an embodiment, processing device 102 is configured to calculate two coordinates for each predefined location on the patient head-"an anatomical point" in a coordinate system of the CT system, and a "position" in a coordinate system of the position tracking system. The anatomical point is derived from the position measurement of wand 112 at the predefined location, and is indicative of the coordinate of the portion of the face at this location in the coordinate system of the magnetic position tracking system. The anatomical point is indicative of the coordinate of the portion of the face, as identified in the CT image 111.

In an embodiment, processing device 102 is configured to correlate the anatomical points and the positions of the predefined locations in image 111, so as to register the CT image with the coordinate system of the position tracking system.

Figure 2:
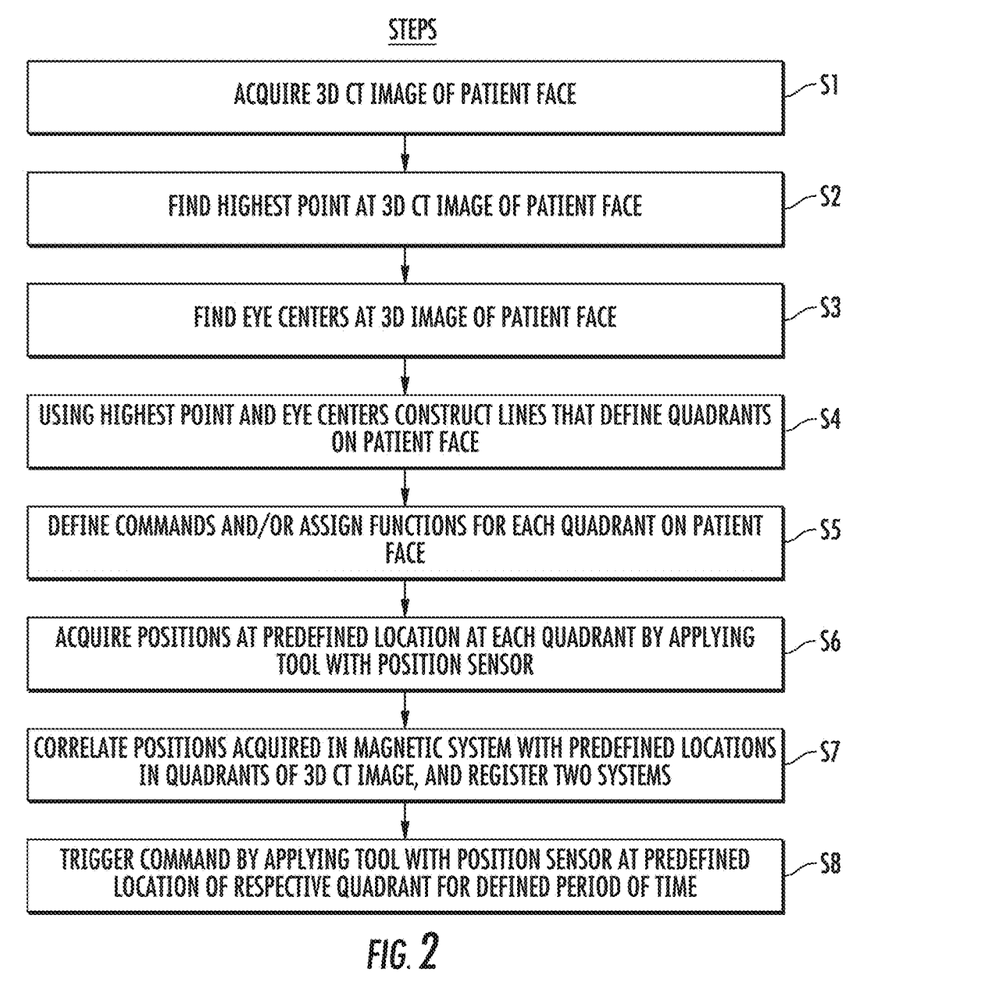
FIG. 2 is a flow chart that schematically illustrates a method for registering a patient face with a coordinate system of magnetic position tracking system and using the patient face as a user interface to control equipment, in accordance with an embodiment of the present invention.

FIG. 2 is a flow chart of the steps of an exemplary method for registering the patient's face with a coordinate system of magnetic tracking system as a user interface to control equipment according to embodiments disclosed herein. FIG. 3 is a schematic drawing of the 3D CT image of the patient face used in the registration method illustrated in FIG. 2. As illustrated in FIG. 2, the method may comprise the step S1 of acquiring an image of the patient face and/or displaying the image on a display screen. The image may be a three-dimensional (3D) ultrasound image, a CT image, MRI image or an image obtained by any other imaging technique known in the art.

In step S2, processing device 102 analyzes the 3D CT image of the patient face 111 as shown in FIG. 3 using image processing software and finds a highest point 192 on the image. Typically, the highest point corresponds to the nose tip of the patient.

In step S3, processing device 102 finds centers 190 and 191 of the eyes of the patient as illustrated in FIG. 3. Methods for finding centers of the eyes are known in the art and are described, for example, in the article entitled "Locating the Eyes of the Patient" published in the Proceedings of the $6^{th}$ International Conference on Industrial and Engineering Applications of Artificial Intelligence and Expert Systems, 1993, pages 507-517, which is incorporated herein by reference as if fully set forth. Other methods for finding the centers of the eyes may also be used.

In step S4, processing device 102 may analyze surface of the 3D image 111 using values acquired in steps S2 and S3 using the image processing software to delineate voxels within the cross-shape (✛) in the acquired image. The cross-shape comprises the bridge of the patient's nose as a vertical line 194 (FIG. 3) of the cross (+). To determine voxels of the vertical line the processor starts from the nose tip (highest point) determined in step S2, and finds other voxels of the bridge of the nose, i.e., the bony section of the nose, by looking for local maxima in surface image 111 in proximity to, and vertically above, the nose tip 192. The processor continues this process iteratively to find voxels corresponding to the complete vertical line 194 of the cross-shape. To find voxels corresponding to a horizontal line 193 of the cross-shape, the processor selects voxels that are a preset vertical distance above a line joining the patient's eye centers, as found in step S3. In one embodiment, the preset distance is 5 cm above the eye center line, but in other embodiments the distance may be larger or smaller than 5 cm. The preset distance is chosen so that the voxels of the horizontal line overlie the bony section of the patient's forehead. The processing device 102 draws line 193 above the line that joins the two eye centers found in step S3. The processing device draws a line 194 orthogonal to line 193 and passing through the highest point on the image of patient face. Typically, both the vertical line and the horizontal line of voxels are more than one voxel wide. As shown in FIG. 3, the two lines divide the image of the face into four quadrants 201 (upper-right quadrant), 202 (upper-left quadrant), 203 (lower-right quadrant) and 204 (lower-left quadrant).

In an image analysis step S4, the processing device 102 may analyze 3D image 111 generated in step S1, using the values acquired in steps S2 and S3. The processing device may generate four subsets of the set of voxels comprising 3D image 111. Each one of the subsets corresponds to respective quadrant of four quadrants 201 (upper-right quadrant), 202 (upper-left quadrant), 203 (lower-right quadrant) and 204 (lower-left quadrant).

In step S5, processing device 102 may define commands and assign functions to each quadrant on the patient face as shown in FIG. 4. The commands may be any commands used during medical procedure. The commands may be commands used during registration or related to registration. For example, touching the lower-right quadrant on the patient's face may be associated with the "Yes" function during the process of registration, while touching the lower-left quadrant may be associated with the "No" function during the registration. The physician may touch the patient's forehead to "Re-Do" the registration. The assigned functions may be stored in a database and may be implemented in the form of logical instructions or commands that are executed by the processing device, such as a computer. The database may be in the form of a registration table. Other commands may also be used. For example, a generic command "Menu" can be used to open additional commands. "Undo" can be used to reverse previous action. "Show"/"Hide" can be used to display or hide content, e.g., images. The commands may be commands for zooming in the 3D CT image, exiting the application or printing the screen.

In step S6, physician 110 may place wand 112 comprising a position sensor at the predefined locations in each of the quadrants of the patient face to acquire the positions in the coordinate system of the position tracking system. In an embodiment, the predefined locations may comprise four points as follows: a point below the tip of the patient's nose, the left and right sides of the patient's face next to the eyes and a point between the eyes. However, fewer than four points, e.g., two points, may be sufficient to generate registration.

In step S7, processing device 102 may correlate the points acquired in step S6 with the subsets of voxels generated in step S4 using the Itirated Closest Point (ICP) algorithm. The algorithm uses the subsets of voxels as the reference set of points, and the positions acquired in step S6 as the source set of points. While performing the correlation the processing device 102 may register between the coordinate systems of the CT and the position tracking systems. The processing device 102 may check if the registration performed in step S7 is sufficiently accurate, i.e., if the errors associated with the cost function generated by the ICP algorithm are sufficiently small, for example, below a preset threshold. If the condition returns positive, then a notice is provided on screen 114 informing the physician 110 that she/he may cease acquiring points. The notice may also suggest that the physician 110 performs a verification of the registration, such as by touching predefined positions and having the processor mark these positions on the CT image, and/or by measuring distances between such positions. If the condition returns negative, or if the verification fails, the physician continues to acquire points with wand 112.

In step S8, the physician 110 may trigger the command by applying a tool equipped with the position sensor in any one of the quadrants of the patient face. The tool may be positioned in the same place of the quadrant for a defined period of time to trigger the command, for example, 2-3 seconds. The tool may have the capability to trigger the command by clicking the position sensor. In response to trigger, the command or function may be communicated to the processing device, which may be a computer.

FIG. 4 is a schematic drawing of the patient face used as a user interface to control equipment in one embodiment. As seen in FIG. 4, the patient's face can be divided into virtual areas, such as quadrants, where a particular virtual area or quadrant is assigned a specific user-defined parameter, or function. Each function corresponds to a command which can be retrieved and performed by the processing device 102.

For example, to indicate whether or not the physician accepts the proposed registration, the physician may input a "Yes" by touching the patient's lower-right quadrant 203, or a "No" by touching the patient's lower-left quadrant 204. The physician may press either the upper-right quadrant 201 or the upper left quadrant 202 of the patient's forehead to "Re-Do" the registration. In an embodiment, processing device 102 is configured to identify each quadrant of the patient face, which corresponds to the specifically assigned function.

In an embodiment, the patient face can be divided into as many virtual sections as necessary to accommodate the physician's needs and to provide functionality as a user interface.

The registration process is performed before the surgical or any other medical procedure performed on the patient. The registration process is typically performed in a non-sterile environment but may also be performed in a sterile environment. The medical procedure may be performed in a sterile environment but with different levels of sterility depending on the setting, e.g., an operating room, office or clinic. During the medical procedure, physician 110 may touch patient face 115 with a medical tool 112 or surgical device, which comprises an additional position sensor of the position tracking system. Since the CT image is already registered with the position-tracking system, physician 110 may apply a medical tool 112 to a pre-defined location on patient face 115 to perform certain actions with a computer. The medical tool may be the wand used for face registration, or any other tool used during the medical procedure. The medical tool may be sterile or non-sterile depending on the type of procedure or setting where the tool is used.

In an embodiment, processing device 102 is configured to receive one or more images using suitable imaging techniques, and to register these anatomical images with the coordinate system as described herein. For example, suitable imaging techniques may be ultrasound, fluoroscopy or magnetic resonance imaging (MRI).

FIG. 1 shows only elements related to the disclosed techniques for clarity and simplicity. System 100 may comprise additional modules and elements that are not directly related to the disclosed techniques, and therefore, these are intentionally omitted from FIG. 1 and from the description thereof.

Processing device 102 may also control other components of the system 100 according to the embodiments described herein. Processing device 102 is preferably programmed in software and/or hardware to perform the functions required by the system. The processing device 102 may store data for the software in a memory. The software may be downloaded to the processing device 102 in electronic form, over a network, or may be provided on tangible media, such as optical, magnetic or other nonvolatile memory media. Alternatively, some or all of the functions of processing device 102 may be performed by dedicated or programmable digital hardware components.

Accordingly, systems and methods have been described that enable utilizing a patient's face as a user interface to facilitate usability of registration equipment. Thus, the proposed system facilitates the usability of equipment during specialized procedures, such as ENT registration procedures, so that the physician can operate the equipment without removing gloves and without assistance from a nurse.

The proposed system facilitates the usability of specialized equipment used in a sterile environment for various medical procedures, such as ENT registrations, when no nurse is present during the procedure. The physician can utilize the patient's face as a user interface to operate the equipment, which enables the physician to overcome the absence of a nurse during the procedure.

It should be understood that many variations are possible based on the disclosure herein. Although features and elements are described above in particular combinations, each feature or element can be used alone without the other features and elements or in various combinations with or without other features and elements.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements the methods described herein.

The methods or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

Certain terminology is used in the description herein for convenience only and is not limiting. The words "right," "left," "top," and "bottom" designate directions in the drawings to which reference is made. The words "a" and "one," as used in the claims and in the corresponding portions of the specification, are defined as including one or more of the referenced items unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

Further embodiments herein may be formed by supplementing an embodiment with one or more elements from any one or more other embodiments herein, and/or substituting one or more elements from one embodiment with one or more elements from one or more other embodiments herein.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A method of utilizing a patient face as a user interface to control equipment, comprising:

acquiring a three-dimensional anatomical image of a patient face and identifying multiple anatomical points corresponding to respective predefined locations on the patient face in a first coordinate system;

assigning at least one function to at least one predefined location on the patient face;

receiving multiple positions in a second coordinate system at the respective predefined locations on the patient face;

registering the first and second coordinate systems, by correlating between the positions and the respective anatomical points on the patient face;

triggering a command corresponding to the at least one assigned function, wherein triggering comprises touching the at least one predefined location on the patient face with a medical tool comprising a position sensor; and communicating the command to an electronic device.

2. The method of claim 1, wherein the three-dimensional anatomical image comprises a computerized tomography image.

3. The method of claim 1, wherein the step of identifying further comprises determining the predefined locations at the three-dimensional anatomical image.

4. The method of claim 3, wherein the step of determining comprises finding the highest point at the three-dimensional anatomical image.

5. The step of claim 4, wherein the step of determining further comprises finding a center in each of the right and left eyes at the three-dimensional anatomical image.

6. The method of claim 5, wherein the step of determining further comprises dividing the three-dimensional anatomical image of patient face into quadrants by two orthogonal lines, wherein the first orthogonal line is above and parallel to a line that connects the center of the right eye and the center of the left eye and the second orthogonal crosses the highest point of the three-dimensional image.

7. The method of claim 1, wherein the multiple anatomical points comprise at least two points at each of the predefined locations.

8. The method of claim 1, wherein the at least one predefined location is selected from the group consisting of: upper-left quadrant, upper-right quadrant, lower-left quadrant and lower-right quadrant of the patient face.

9. The method of claim 1, wherein receiving the multiple positions comprises receiving the positions from a registration tool comprising a position sensor.

10. The method of claim 1, wherein receiving the multiple positions comprises receiving the positions from scanning the patient face with a three-dimensional scanner.

11. The method of claim 1, wherein the electronic device is a computer.

12. A system for utilizing a patient face as a user interface, comprising:
a registration tool, which comprises a position sensor of a position-tracking system, which is configured to acquire multiple positions in a second coordination system by positioning the registration tool at respective predefined locations on a patient face;
a medical tool, which comprises a position sensor, and which is configured to trigger a command by touching at least one predefined location on the patient face; and
a processor, which is configured to:
identify, in a three-dimensional anatomical image of the patient face, multiple anatomical points corresponding to the respective predefined locations in a first coordinate system;
assign at least one function to at least one predefined location on the patient face;
receive the multiple positions measured in the second coordinate system;
register the first and second coordinate systems, by correlating between the positions and the respective anatomical points on the patient face; and
retrieve a command corresponding to the at least one assigned functions.

13. The system of claim 12, wherein the three-dimensional anatomical image comprises a computerized tomography image.

14. The system of claim 12, wherein the three-dimensional anatomical image comprises a three-dimensional scan.

15. The system of claim 12, wherein the processor is further configured to determine the predefined locations at the three-dimensional anatomical image, wherein the step of determining comprises:
finding the highest point at the three-dimensional anatomical image;
finding a center in each of the right and left eyes at the three-dimensional anatomical image; and
dividing the three-dimensional anatomical image of patient face into quadrants by two orthogonal lines, wherein the first orthogonal line is above and parallel to a line that connects the center of the right eye and the center of the left eye and the second orthogonal crosses the highest point of the three-dimensional image.

16. The system of claim 12, wherein the predefined location is selected from the group consisting of: upper-left quadrant, upper-right quadrant, lower-left quadrant and lower-right quadrant of the patient face.

17. A method, comprising:
acquiring a three-dimensional anatomical image of a patient face and identifying multiple anatomical points on the three-dimensional image corresponding to respective predefined locations on the patient face in a first coordinate system, wherein the step of identifying comprises determining the predefined locations at the three-dimensional anatomical image and finding the highest point at the three-dimensional anatomical image;
assigning at least one function to at least one predefined location on the patient face;
receiving multiple positions in a second coordinate system at the respective predefined locations on the patient face;
registering the first and second coordinate systems, by correlating between the positions and the respective anatomical points on the patient face;
triggering a command corresponding to the at least one assigned function; and
communicating the command to an electronic device.

18. The step of claim 17, wherein the step of determining further comprises finding a center in each of the right and left eyes at the three-dimensional anatomical image.

19. The method of claim 17, wherein the step of determining further comprises dividing the three-dimensional anatomical image of patient face into quadrants by two orthogonal lines, wherein the first orthogonal line is above and parallel to a line that connects the center of the right eye and the center of the left eye and the second orthogonal crosses the highest point of the three-dimensional image.

* * * * *

UNITED STATES PATENT AND TRADEMARK OFFICE
CERTIFICATE OF CORRECTION

| | |
|---|---|
| PATENT NO. | : 10,452,263 B2 |
| APPLICATION NO. | : 15/703418 |
| DATED | : October 22, 2019 |
| INVENTOR(S) | : Moshe Ingel et al. |

It is certified that error appears in the above-identified patent and that said Letters Patent is hereby corrected as shown below:

On the Title Page

In Item (72), under "Inventors", in Column 1, Line 2, delete "Kafar Misr" and insert -- Kafr Misr --, therefor.

In the Specification

In Column 5, Line 2, delete "." and insert -- (+). --, therefor.
In Column 6, Line 6, delete "Itirated" and insert -- Iterative --, therefor.

In the Claims

In Column 9, Line 1, in Claim 5, delete "step" and insert -- method --, therefor.
In Column 10, Line 42, in Claim 18, delete "step" and insert -- method --, therefor.

Signed and Sealed this
Twenty-second Day of November, 2022

Katherine Kelly Vidal
*Director of the United States Patent and Trademark Office*